(12) United States Patent
Duan et al.

(10) Patent No.: US 12,152,245 B2
(45) Date of Patent: Nov. 26, 2024

(54) NUCLEIC ACID APTAMER SPECIFICALLY RECOGNIZING β-LACTOGLOBULIN AND USE THEREOF

(71) Applicant: JIANGNAN UNIVERSITY, Wuxi (CN)

(72) Inventors: Nuo Duan, Wuxi (CN); Shijia Wu, Wuxi (CN); Shuo Qi, Wuxi (CN); Zhouping Wang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 795 days.

(21) Appl. No.: 17/416,490

(22) PCT Filed: Jun. 24, 2020

(86) PCT No.: PCT/CN2020/097954
§ 371 (c)(1),
(2) Date: Jun. 20, 2021

(87) PCT Pub. No.: WO2021/159650
PCT Pub. Date: Aug. 19, 2021

(65) Prior Publication Data
US 2022/0340905 A1    Oct. 27, 2022

(30) Foreign Application Priority Data
Feb. 15, 2020   (CN) .......................... 202010094212.6

(51) Int. Cl.
*C12N 15/115* (2010.01)
*G01N 33/68* (2006.01)

(52) U.S. Cl.
CPC ............ *C12N 15/115* (2013.01); *G01N 33/68* (2013.01); *C12N 2310/16* (2013.01); *G01N 2333/4713* (2013.01)

(58) Field of Classification Search
CPC .. C12N 15/115; C12N 2310/16; G01N 33/68; G01N 2333/4713
See application file for complete search history.

(56) References Cited

FOREIGN PATENT DOCUMENTS

| CN | 106645050 A | | 5/2017 |
|---|---|---|---|
| CN | 107607722 A | | 1/2018 |
| CN | 109507423 A | * | 3/2019 |
| CN | 111172166 A | | 5/2020 |
| WO | 2018089391 A1 | | 5/2018 |

OTHER PUBLICATIONS

Yu et al., "Selection of aptamers against Lactoferrin based on silver enhanced and fluorescence-activated cell sorting" Talanta 193 (2019) 110-117 (Sep. 19, 2018).
He et al., "Research progress on the detection methods of cow's milk allergen β-lactoglobulin" Journal of Food Safety and Quality, vol. 10, No. 7, Apr. 2019, pp. 1763-1769 (Apr. 30, 2019).

\* cited by examiner

*Primary Examiner* — Shin Lin Chen
*Assistant Examiner* — Gillian C. Reglas
(74) *Attorney, Agent, or Firm* — SZDC Law PC (57) ABSTRACT

The present invention provides a nucleic acid aptamer specifically recognizing β-lactoglobulin and use thereof. The nucleic acid aptamer has a sequence as shown in SEQ ID NO:1, a sequence having 60% or higher homology to the sequence as shown in SEQ ID NO:1 and specifically recognizing β-lactoglobulin, or a sequence derived from the sequence as shown in SEQ ID NO:1 and specifically recognizing β-lactoglobulin. The nucleic acid aptamer specifically binds to the allergen β-lactoglobulin in cow milk and dairy products, thereby providing a new tool for the high-sensitivity and low-cost detection of the allergen β-lactoglobulin.

5 Claims, 6 Drawing Sheets
Specification includes a Sequence Listing.

SEQUENCE LISTING

```
<160> NUMBER OF SEQ ID NOS: 3

<210> SEQ ID NO 1
<211> LENGTH: 80
<212> TYPE: DNA
<213> ORGANISM: Artificial sequence
<220> FEATURE:
<223> OTHER INFORMATION: Aptamer Lg-18

<400> SEQUENCE: 1
agcagcacag aggtcagatg ttcggccttt gcgttaacga acttctagct atgcggcgta    60
cctatgcgtg ctaccgtgaa                                                80

<210> SEQ ID NO 2
<211> LENGTH: 80
<212> TYPE: DNA
<213> ORGANISM: Artificial sequence
```

```
<220> FEATURE:
<223> OTHER INFORMATION: Aptamer Lg-9

<400> SEQUENCE: 2
agcagcacag aggtcagatg gttttgttgg gtctgctacg gactttgttg acctttgctc    60
cctatgcgtg ctaccgtgaa                                               80

<210> SEQ ID NO 3
<211> LENGTH: 79
<212> TYPE: DNA
<213> ORGANISM: Artificial sequence
<220> FEATURE:
<223> OTHER INFORMATION: Aptamer Lg-16

<400> SEQUENCE: 3
agcagcacag aggtcagatg tcgtttgtgg ctgtcaattg gtgtgtttac ctgttttggc    60
ctatgcgtgc taccgtgaa                                                79
```

NUCLEIC ACID APTAMER SPECIFICALLY RECOGNIZING β-LACTOGLOBULIN AND USE THEREOF

This application is the National Stage Application of PCT/CN2020/097954, filed on Jun. 24, 2020, which claims priority to Chinese Patent Application No. 202010094212.6, filed on Feb. 15, 2020, which is incorporated by reference for all purposes as if fully set forth herein.

A Sequence Listing ASCII text file named "20210620_10015_0068_Sequence_Listing.txt" created on Jun. 20, 2021 and having a size of 1,010 bytes, is filed concurrently with the specification. The sequence listing contained in the ASCII text file is part of the specification and is herein incorporated by reference in its entirety.

FIELD OF THE INVENTION

The present invention relates to the technical field of biology and medicines and particularly to a nucleic acid aptamer specifically recognizing β-lactoglobulin and use thereof.

DESCRIPTION OF THE RELATED ART

Food allergy is an adverse reaction of some people to certain foods (including IgE-mediated and non-IgE-mediated immune reactions). Food allergies not only seriously affect the quality of life of patients, but also cause malnutrition and health problems in patients, such as asthma, gastrointestinal and skin inflammations. In severe cases, life-threatening anaphylactic shock may be caused.

Cow milk and dairy products have gradually become an important part in healthy diets of human beings because they contain essential amino acids and rich minerals. However, as one of the eight categories of allergic foods designated by the World Health Organization (WHO) and the Food and Agriculture Organization (FAO) of the United Nations, cow milk and dairy products contain a variety of allergenic proteins (αs1-casein, α-lactalbumin and β-lactoglobulin etc.) seriously affecting the health of some people. Epidemiological surveys show that up to 8% of infants and 1%-2% of adults are allergic to milk. In recent years, due to the changes in lifestyle, microbial exposure, changes in eating habits and other factors, the immune function of intestinal tract of infants is getting lower and lower, and the incidence of milk allergy in infants becomes increasingly higher year by year.

β-lactoglobulin accounts for about 10% of cow milk protein content and about 50% of total whey protein. Human milk does not contain β-lactoglobulin. About 82% of patients with IgE-mediated cow milk allergy are allergic to β-Lactoglobulin, so β-lactoglobulin is considered to be the main allergen in cow milk. The highly sensitive detection of the allergen β-lactoglobulin in cow milk and dairy products is of great significance for providing necessary dietary guidance for allergic populations.

At present, the commonly used methods for the analysis and detection of milk allergens in food include: (1) high performance liquid chromatography (HPLC) based on chromatographic analysis, which, however, has the disadvantages that the instrument is expensive, the usage scenario is limited, and the cost is high; (2) fluorescence quantitative PCR (qPCR) and loop-mediated isothermal amplification based on the identification of characteristic genes, which, however, has the problem of poor specificity and complicated operation; and (3) enzyme-linked immunosorbent assay (ELISA) based on specific recognition by antibodies, which, however, is difficult to analyze allergens in food with low cost and high sensitivity since the antibodies are proteins, and has poor stability and low sensitivity.

Nucleic acid aptamer is a single-stranded oligonucleotide able to specifically bind to a target substance, and is obtained by screening from an artificially synthesized random nucleotide library by systematic evolution of ligands by exponential enrichment (SELEX). As a new type of "antibody", the aptamer is formed to have a specific three-dimensional conformation (hairpin, pseudoknot, bulge and G-quadruplex, etc.). By means of spatial structure matching, hydrogen bonding, van der Waals force, electrostatic interactions, and other intermolecular interactions, the aptamer binds to a target substance with high-affinity. Compared with antibodies, the aptamer has many advantages: (1) artificial synthesis independent of animal immunity, and small differences between batches. (2) good stability, long-term storage, and high heat resistance; (3) high affinity, high specificity, and a Kd of the aptamer as low as nanomolar level, enabling a good distinguishment of structural analogues; and (4) easy modification, where the aptamer is labeled with a chemical group (such as FAM, ROX, FITC and biotin, etc.) at both ends, which does not affect its affinity, and can expand its scope of application, thus being widely used in detection techniques based on recognition by an aptamer.

TECHNICAL PROBLEM

Mohammed Zourob et al. provides a nucleic acid aptamer binding β-lactoglobulin in an English literature, and constructs an electrochemical detection solution therewith. In the literature, β-lactoglobulin is immobilized on agarose microspheres by a target immobilization method to screen a nucleic acid aptamer enriching β-lactoglobulin. During detection, the nucleic acid aptamer is adsorbed on graphene oxide. When β-lactoglobulin is present, the nucleic acid aptamer specifically binds it and falls off from the graphene oxide, causing changes in electrochemical signals. The disadvantage of this solution is that the aptamer has a large Kd and the specificity of the aptamer has not been studied. There are too many interference factors in the detection of an actual sample, the detection limit is high, and the binding mechanism of aptamer with β-lactoglobulin is not clear.

SUMMARY OF THE INVENTION

Technical Solution

To solve the above technical problems, an object of the present invention is to provide a nucleic acid aptamer specifically recognizing β-lactoglobulin and use thereof. The nucleic acid aptamer can specifically bind to the allergen β-lactoglobulin in cow milk and dairy products, and is a new type of recognition molecule for the high-sensitivity and low-cost detection of allergen β-lactoglobulin. Therefore, the present invention solves the problems existing in current detection processes of allergen β-lactoglobulin that the cost is high and the applicability is largely limited because of the relying on chromatographic equipment, and the repeatability is poor due to the dependence on the stability of antibodies; and provides a new tool for the detection solution for the allergen β-lactoglobulin in cow milk and dairy products.

The following technical solution is adopted in the present invention.

A first object of the present invention is to provide a nucleic acid aptamer specifically recognizing β-lactoglobulin. The nucleic acid aptamer has a sequence as shown in SEQ ID NO:1, a sequence having 60% or higher homology to the sequence as shown in SEQ ID NO:1 and specifically recognizing β-lactoglobulin, or a sequence derived from the sequence as shown in SEQ ID NO:1 and specifically recognizing β-lactoglobulin.

Preferably, the nucleotide sequence of the nucleic acid aptamer is modified by any one or more of phosphorylation, methylation, amination, sulfhydrylation, phosphorothioate modification, and side chain modification of glycosyl ring.

Preferably, the nucleotide sequence of the nucleic acid aptamer is linked with any one or more of a fluorescent marker, a radioactive material, a therapeutic material, biotin, digoxin, a nano-luminescent material, a small peptide, siRNA and an enzyme marker.

Preferably, the sequence as shown in SEQ ID NO:1 has an intermolecular interaction with β-lactoglobulin, where hydrogen bonding is formed between C-45/T-46 and ARG-40, G-56 and SER-36, C-57 and ASN-63, G-58 and ASN-63/TRP-61, and G-76 and SER-30.

A second object of the present invention is to provide a kit including the nucleic acid aptamer.

A third object of the present invention is to provide use of the nucleic acid aptamer in the detection of β-lactoglobulin. A standard curve for the detection of β-lactoglobulin by the nucleic acid aptamer is plotted by a method including the steps of:

(1) construction of a recognition probe, including: uniformly mixing the nucleic acid aptamer and a complementary short chain thereof at a molar ratio of 1:1, and then denaturing;

(2) construction of a beacon hairpin molecule, including: dissolving a beacon hairpin molecule in a binding buffer and then denaturing;

(3) enzymatic digestion and cyclic amplification, including: mixing the recognition probe, the beacon hairpin molecule and exonuclease III uniformly, co-incubating with various concentrations of standard β-lactoglobulin solutions for 2-3 h, and determining the fluorescence intensity by a fluorescence spectrometer at an excitation wavelength of 575 nm and an emission wavelength of 606 nm; and (4) plotting of a standard detection curve, comprising: according to the changes in the intensity of the fluorescence signal at various concentrations of β-lactoglobulin, plotting a standard curve for detecting β-lactoglobulin by the nucleic acid aptamer with the logarithm of the concentration of β-lactoglobulin as a horizontal ordinate and the fluorescence intensity as a vertical ordinate.

Preferably, in the step (2), the beacon hairpin molecule is denatured at 95° C. for 10 min, and then gradually cooled to 37° C. for 3 h.

Preferably, in the step (3), the incubation time is 2 h, and the volume of the incubation system is 400 μL; the concentration of the beacon hairpin molecule is 400 nM, and the enzyme activity of the exonuclease III is 0.25 U/μL.

Preferably, in the step (3), the molar ratio of the recognition probe to the beacon hairpin molecule is 1:2.

Beneficial Effects (1) Compared with the previous target immobilization technology for screening a nucleic acid aptamer of a protein, an aptamer binding β-lactoglobulin is screened by a library immobilization method in the present invention, which effectively overcomes the steric hindrance effect associated with a conventional method and the defect of conformational change caused by target immobilization.

(2) The present invention provides an aptamer specifically recognizing the allergen β-lactoglobulin in cow milk and dairy products. It has been verified that the aptamer can bind to the allergen β-lactoglobulin with a dissociation constant below 100 nM (as shown in Table 1) and well distinguish proteins (α-lactalbumin, and casein) and structural analogs (IgG, and bovine serum albumin), thus having good affinity and specificity.

(3) The nucleic acid aptamer can be labeled with FAM, FITC or biotin at the 5' or 3' terminus, can realize the rapid qualitative and quantitative detection of the allergen β-lactoglobulin, and has the advantages of low cost, high specificity and wide scope of application. The nucleic acid aptamer specifically recognizing the allergen β-lactoglobulin in cow milk and dairy products provided in the present invention, as an allergen recognition molecule, is considered to be a very useful tool in the fields of food processing, food management and nutritional programming.

(4) The nucleic acid aptamer has a typical stem-loop structure in the secondary structure of the nucleotide sequence, indicating that the aptamer has a good stability. The binding of the aptamer to a target depends on the secondary structure of the aptamer which is the stem-loop structure in one case. The formation of the stem-loop structure is the structural basis for the affinity of the aptamer.

(5) In the present invention, the three-dimensional conformation of the nucleic acid aptamer is constructed. The interaction between the nucleic acid aptamer and the allergen β-lactoglobulin is simulated by molecular docking, to explore the binding mode of the nucleic acid aptamer and β-lactoglobulin and explain the internal cause underlying the high affinity of the nucleic acid aptamer for the allergen β-lactoglobulin, which provides a better theoretical guidance for the subsequent optimization of the aptamer binding the allergen β-lactoglobulin.

DETAILED DESCRIPTION OF THE PREFERRED EMBODIMENTS

Hereinafter, the embodiments of the present invention will be described in detail by way of examples. However, it should be understood by those skilled in the art that the following examples are for illustrative purposes and not intended to limit the scope of the invention in any way.

Where no specific conditions are given in the examples, conventional conditions or conditions recommended by the manufacturer are followed. The reagents or instruments for which no manufacturers are noted are all common products commercially available from the market.

Example 1

Design and Synthesis of Large Single-Stranded Oligonucleotide Library and Primers A library of single-stranded oligonucleotides with a length of 80 nt having a library size of up to $10^{12}$-$10^{24}$ was constructed, where the single-stranded oligonucleotide has a random sequence region of 40 nt in the middle (determining the richness of the library) and a constant sequence region of 20 nt at both ends (a sequence necessary for primer binding). Sequence: 5'-AGCAGCACAGAGGTCAGATG-40 random base-CCTATGCGTGCTACCGTGAA-3', synthesized by Dalian TaKaRa Bio Co., Ltd.

```
Forward primer:
5'-FAM-AGCAGCACAGAGGTCAGATG-3'

Reverse primer:
5'-P-TTCACGGTAGCACGCATAGG-3'

Biotinylated complementary short chain:
5'-Biotin-AGCACGCATAGG-3'
```

The primers were synthesized by Sangon Biotech (Shanghai) Co., Ltd.

The single-stranded oligonucleotide library and primers were all prepared with TE buffer into 100 μM stock solutions and stored at −20° C. for later use.

Example 2

Screening of Aptamer Binding Allergen β-Lactoglobulin Based on Capture-SELEX Technology First, the single-stranded oligonucleotide library was hybridized with the biotinylated complementary short chain, then immobilized on streptavidin-coupled magnetic beads and co-incubated with the allergen β-lactoglobulin. Single-stranded nucleic acid fell off from the magnetic beads due to the interaction with β-lactoglobulin and were released into the solution. After incubation, the supernatant was used as a template of a secondary library for PCR amplification. The amplified product was enzymatically digested, to produce single strands, which were precipitated in ethanol to obtain the secondary library for the next round of screening. The specific steps were as follows.

Hybridization of single-stranded oligonucleotide library with biotinylated complementary short chain: The ssDNA library was mixed with the biotinylated complementary short chain at a ratio of 1:1.5 (where the amount of the single-stranded oligonucleotide library used in the first round of screening was 1 nmol, and the amount of the secondary library used in other rounds was 100 pmol), denatured at 95° C. for 10 min, and then slowly cooled to 37° C. for 3 h until the two were fully hybridized.

Immobilization of single-stranded oligonucleotide library: The hybridized mixture was reacted with a certain amount of streptavidin-coupled magnetic beads (where the weight ratio of the nucleic acid library to magnetic beads was 1:400) at 37° C. and 200 rpm for 2 h to immobilize the single-stranded oligonucleotide library on the magnetic beads by the strong binding between the biotin and streptavidin.

Target incubation: The immobilized single-stranded nucleotide library was incubated with 50 μg/mL β-lactoglobulin in a 300 μL system at 37° C. and 200 rpm, and the relative fluorescence enrichment rate of each screening cycle was calculated. According to the results of fluorescence monitoring during the screening process, in the sixth and tenth rounds, a counter screening process was added. Before incubation with the target, coexisting substances (α-lactalbumin, and casein) and structural analogs (BSA, and IgG) were introduced into the system to increase the screening stress to obtain sequences with better affinity and specificity.

PCR amplification and verification: After magnetic separation, the supernatant after incubation with the target was obtained, which was used as a template for PCR amplification. Amplification system: 1 μL template, 0.5 μL Taq DNA polymerase (5 U/μL), 5 μL 10× polymerase buffer (containing 20 mM $MgCl_2$), 0.5 μL forward and reverse primers, 1 μL dNTP Mix (5 mM), and 42 μL dd$H_2O$. Amplification procedure includes pre-denaturation at 95° C. for 5 min, 10 cycles of denaturation at 95° C. for 30 s, annealing at 58° C. for 30 s, and extension at 72° C. for 30 s, and final extension at 72° C. for 5 min, and storage at 4° C. After verification by 8% non-denaturing polyacrylamide gel electrophoresis, whether the electrophoresis band is single and bright and whether the band is at the 80 bp were observed to ensure the success of the PCR amplification of the template.

Preparation of secondary library of single-stranded oligonucleotide: After the amplified product was purified, the antisense strand of the phosphorylated PCR product was specifically digested with lambda exonuclease to prepare single strands. The digestion conditions included 350 μL PCR amplified product, 35 μL exonuclease buffer, 2 μL lambda exonuclease, and reaction at 37° C. The digestion process was determined by electrophoresis on 8% denaturing polyacrylamide gel (containing 7M urea). When the reaction was over, the reaction was terminated by inactivating the enzyme at 75° C. for 10 min. After phenol/chloroform purification and ethanol precipitation, a secondary library of single-stranded oligonucleotides was obtained.

Figure 1:
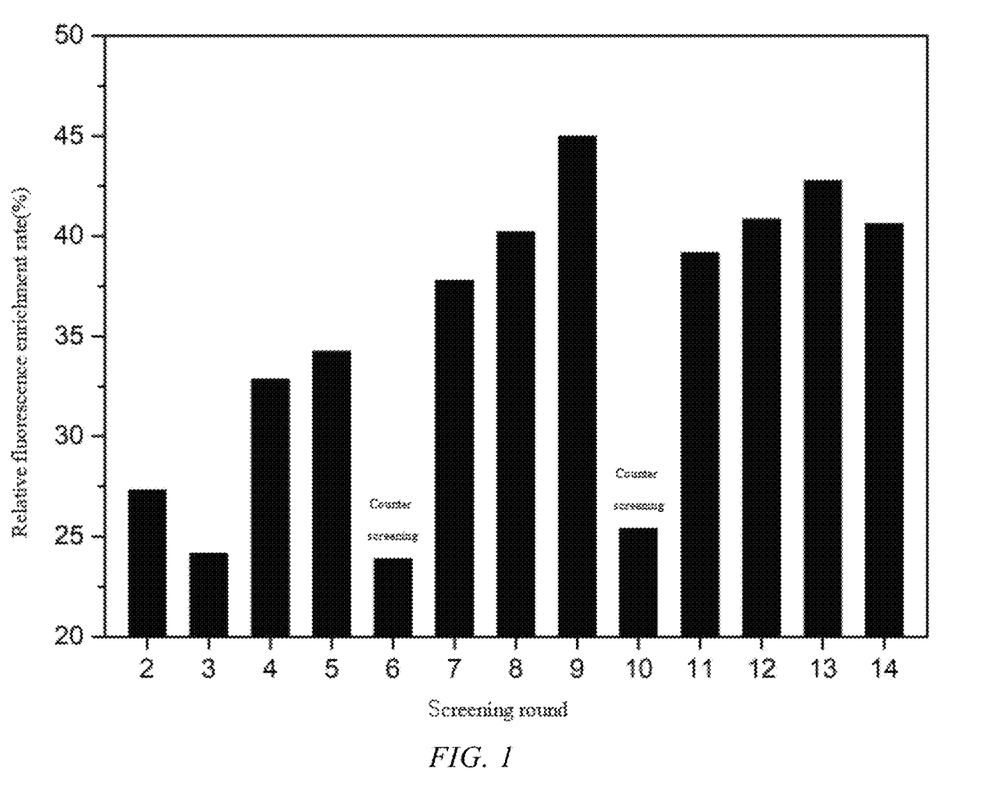
FIG. 1 shows the change of fluorescence enrichment rate during the screening of a nucleic acid aptamer in Example 2.

Cloning and sequencing: According to the fluorescence enrichment rate during the screening process (as shown in FIG. 1), relatively saturated round 13 with a fluorescence enrichment rate of 42.77% was taken as the end point of the screening. The screened single-stranded oligonucleotides were amplified by PCR using unlabeled forward and reverse primers, and then shipped to General Biosystems, Inc. for TA cloning and sequencing. The screened single-stranded oligonucleotides were analyzed for the homology by DNA-MAN software and for the secondary structure by Mfold online tool. 40 sequences were divided into 7 families, and 1-2 sequences from each family were selected as to-beanalyzed candidate aptamer sequences according to the free energy of secondary structure and the homology.

Example 3

Affinity and Specificity Analysis (1) Affinity Analysis Based on Isothermal Titration Calorimetry (ITC)

PEAQ-ITC (Malvern Instruments Co., Ltd.) was used to analyze the binding ability of 10 candidate sequences. 300 μL of β-lactoglobulin solution (6 μM) was injected into the sample cell, and 38 μL of the candidate sequence solution (100 μM) was taken by the injection needle. The program was set such that the volume of the initial first drop titrated by the injection needle was 0.4 μL (to avoid the reaction of the sample in the top of the injection needle with the sample in the sample cell to affect the final result). Then 18 drops were injected and each drop was 2 μL, with an interval of 150 s. The rotation speed of the injection needle was 750 rpm to ensure sufficient reaction upon each injection. At the same time, the dilution heat caused by the titration of the buffer into the β-lactoglobulin solution was eliminated. The binding force and thermodynamic parameters in the binding process were obtained by fitting in the PEAQ-ITC analysis software.

The buffer used in the isothermal titration calorimetry (ITC) was 10 mM Tris-HCl, pH 7.4.

As a result, it was found that the aptamer (Lg-18) has the best ability of binding to β-lactoglobulin. The sequence of the aptamer (Lg-18) is shown below.

```
Lg-18 (SEQ ID NO: 1):
AGCAGCACAGAGGTCAGATGTTCGGCCTTTGCGTTAACGAACTTCTAG

CTATGCGGCGTACCTATGCGTGCTACCGTGAA
```

Figure 2:
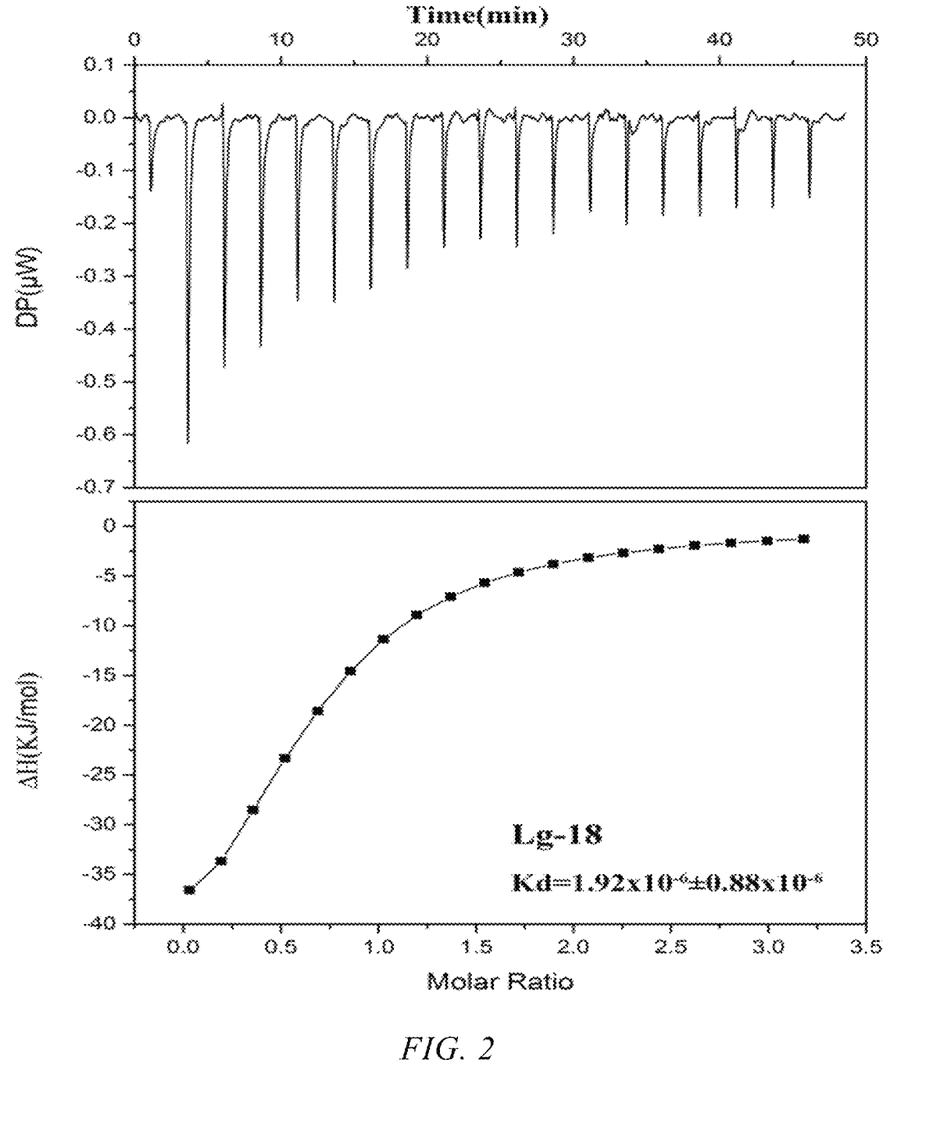
FIG. 2 shows a calorimetric curve of the nucleic acid aptamer Lg-18 in Example 3.

The analysis result by ITC of the aptamer (Lg-18) is shown in FIG. 2. It can be seen from FIG. 2 that the nucleic acid aptamer Lg-18 has a good binding ability to β-lactoglobulin.

In the upper panel of FIG. 2, the horizontal ordinate is time and the vertical ordinate is thermal power. The peak area between the peak base and the peak top is the total heat released during each titration.

In the lower panel of FIG. 2, the horizontal ordinate is the molar ratio of the titrant to the sample solution, and the vertical ordinate is the total heat generated by the titration.

In addition, the homologous sequences (Lg-9 and Lg-16) of the aptamer Lg-18 also have good ability of binding to β-lactoglobulin.

The sequences of Lg-9 and Lg-16 were as follows:

```
Lg-9 (SEQ ID NO: 2):
AGCAGCACAGAGGTCAGATGGTTTTGTTGGGTCTGCTACGGACTTTGT

TGACCTTTGCTCCCTATGCGTGCTACCGTGAA

Lg-16 (SEQ ID NO: 3):
AGCAGCACAGAGGTCAGATGTCGTTTGTGGCTGTCAATTGGTGTGTTT

ACCTGTTTTGGCCTATGCGTGCTACCGTGAA
```

(2) Affinity and Specificity Analysis of Aptamer Recognition Based on Magnetic Separation The aptamers used were Lg-18, Lg-9, and Lg-16 where the sequence was modified with a FAM fluorophore or other fluorescent molecules at the 5' terminal.

Figure 3:
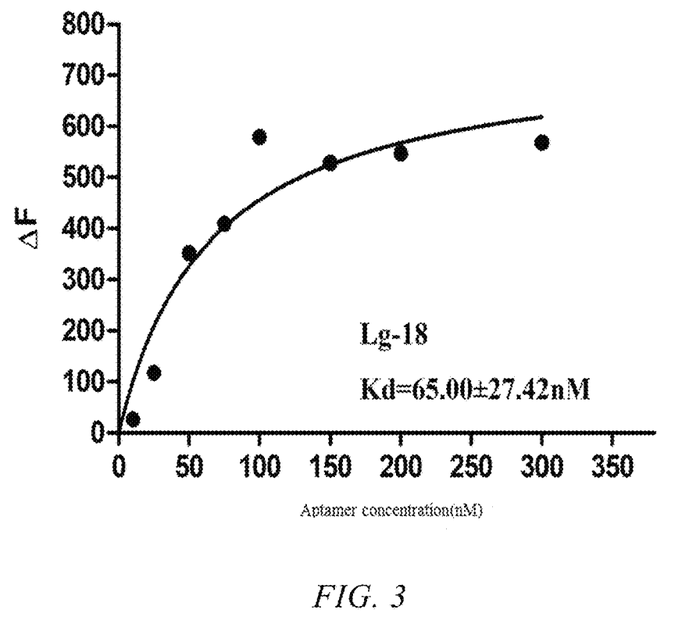
FIG. 3 shows a binding saturation curve of the nucleic acid aptamer Lg-18 in a fluorescence method in Example 3.

Various concentrations (10 nM, 25 nM, 50 nM, 75 nM, 100 nM, 150 nM, 200 nM, and 300 nM) of the aptamer were respectively mixed with the biotinylated complementary short chain at a molar ratio of 1:1.5, denatured at 95° C. for 10 min, and slowly cooled to 37° C. for 3 h until the two were fully hybridized. The mixture was reacted with a certain amount of streptavidin-coupled magnetic beads (where the weight ratio of the aptamer to the magnetic beads was 1:400) at 37° C. and 200 rpm for 2 h to immobilize the aptamer on the magnetic beads by the strong binding between the biotin and streptavidin. The immobilized magnetic beads were incubated with 50 μg/mL β-lactoglobulin in a 300 μL system at 37° C. and 200 rpm. After magnetic separation, the supernatant was subjected to fluorescence measurement at an excitation wavelength of 485 nm and an emission wavelength of 522 nm. The relative fluorescence intensity at various aptamer concentrations was nonlinearly fitted by GraphPad prism 5.0 software, and the dissociation constant Kd of the aptamer was calculated (see Table 1). FIG. 3 shows a saturation binding curve of Lg-18. It can be seen from Table 1 that the Kd of Lg-18 is the smallest, and is 65.00±27.42 nM, indicating that the aptamer Lg-18 has the best binding performance. The homologous sequences (Lg-9 and Lg-16) of the aptamer Lg-18 also have good ability of binding to β-lactoglobulin.

Figure 4:
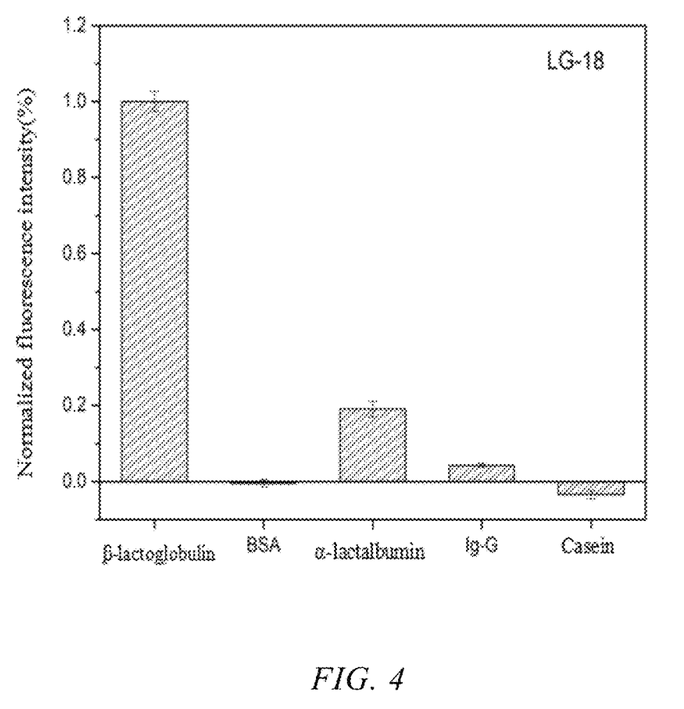
FIG. 4 characterizes the nucleic acid aptamer Lg-18 specifically binding a target in Example 3.

The specificity of the aptamer (Lg-18) was evaluated by the same method. 200 nM aptamer was immobilized on the magnetic beads and incubated respectively with 50 μg/mL coexisting substances (α-lactalbumin and casein) and structural analogues (BSA and IgG). After magnetic separation, the fluorescence intensity of the supernatant was measured respectively, and then the specificity of the aptamer was evaluated. The results are shown in FIG. 4, indicating that the aptamer (Lg-18) has good specificity.

TABLE 1

| Sequence | Dissociation constant Kd (nM) |
| --- | --- |
| Lg-9 | 71.85 ± 16.06 |
| Lg-16 | 65.85 ± 15.16 |
| Lg-18 | 65.00 ± 27.42 |

Example 4

Sensitive Detection and Analysis of β-Lactoglobulin Based on Recognition by Nucleic Acid Aptamer Construction of a recognition probe (Lg-18): The nucleic acid aptamer was uniformly mixed with the complementary short chain thereof at a molar ratio of 1:1, denatured at 95° C. for 10 min, and then slowly cooled to 37° C. for 3 h until the two were fully hybridized.

Construction of a beacon hairpin molecule: A beacon hairpin molecule was dissolved in a binding buffer (100 mM NaCl, pH7.4), denatured at 95° C. for 10 min, and then gradually cooled to 37° C. for 3 h to ensure that a hairpin structure was fully formed.

```
Beacon hairpin molecule:
5'-ROX-ACCTCTGTATCGACATTCACAGAGGT-

BHQ2 (labeled on base T)-CAGATGTT-3'
```

Enzymatic digestion and cyclic amplification: The recognition probe (200 nM), the beacon hairpin molecule (400 nM) and exonuclease III (0.25 U/μL) were uniformly mixed and co-incubated respectively with various concentrations (20 ng/mL, 50 ng/mL, 100 ng/mL, 200 ng/mL, 500 ng/mL, 1000 ng/mL, 2000 ng/mL, and 5000 ng/mL) of standard β-lactoglobulin solutions for 2 h in an incubation system of 400 μL. When to-be-detected β-lactoglobulin was present in the system, due to the stronger binding between the nucleic acid aptamer and β-lactoglobulin than the interaction between the aptamer and the complementary short chain, the complementary short chain fell off from the aptamer, and bound to the 3' terminus of the beacon hairpin molecule to form a double-stranded region. Therefore, the beacon hairpin molecule was opened and the fluorescence was restored. At the same time, the exonuclease III in the system acted on the double-stranded region, to digest the single-stranded oligonucleotide along the 3'-5' of the beacon hairpin molecule, so that the complementary short chain was released and recycled, and the fluorescence signal was further enhanced. F7000 fluorescence spectrometer was used for fluorescence measurement at an excitation wavelength of 575 nm and an emission wavelength of 606 nm.

Figure 5:
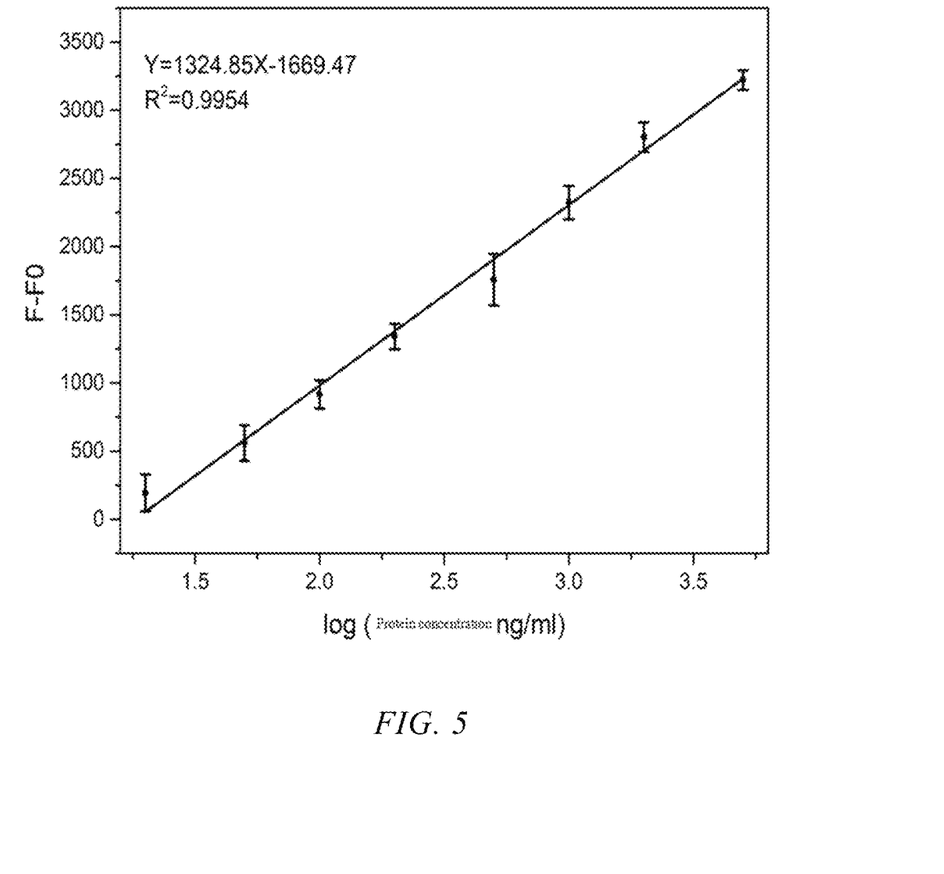
FIG. 5 shows a standard curve of a biosensor constructed with the nucleic acid aptamer Lg-18 in Example 4 for the detection of the allergen β-lactoglobulin.

Plotting of a standard detection curve: According to the changes in the intensity of the fluorescence signals at various concentrations of β-lactoglobulin, a standard curve for the sensitive detection of β-lactoglobulin based on recognition by the aptamer with the logarithm of the concentration of β-lactoglobulin as a horizontal ordinate and the fluorescence intensity as a vertical ordinate was plotted, as shown in FIG. 5. Standard curve: Y=1324.85X−1669.47, R2=0.9954. Linear detection range: 20 ng/mL-5 μg/mL, Limit of detection (LOD): 1.02 ng/mL.

Example 5

Analysis of the Secondary Structure of the Aptamer (Lg-18) by Mfold Online Tool

Figure 6:
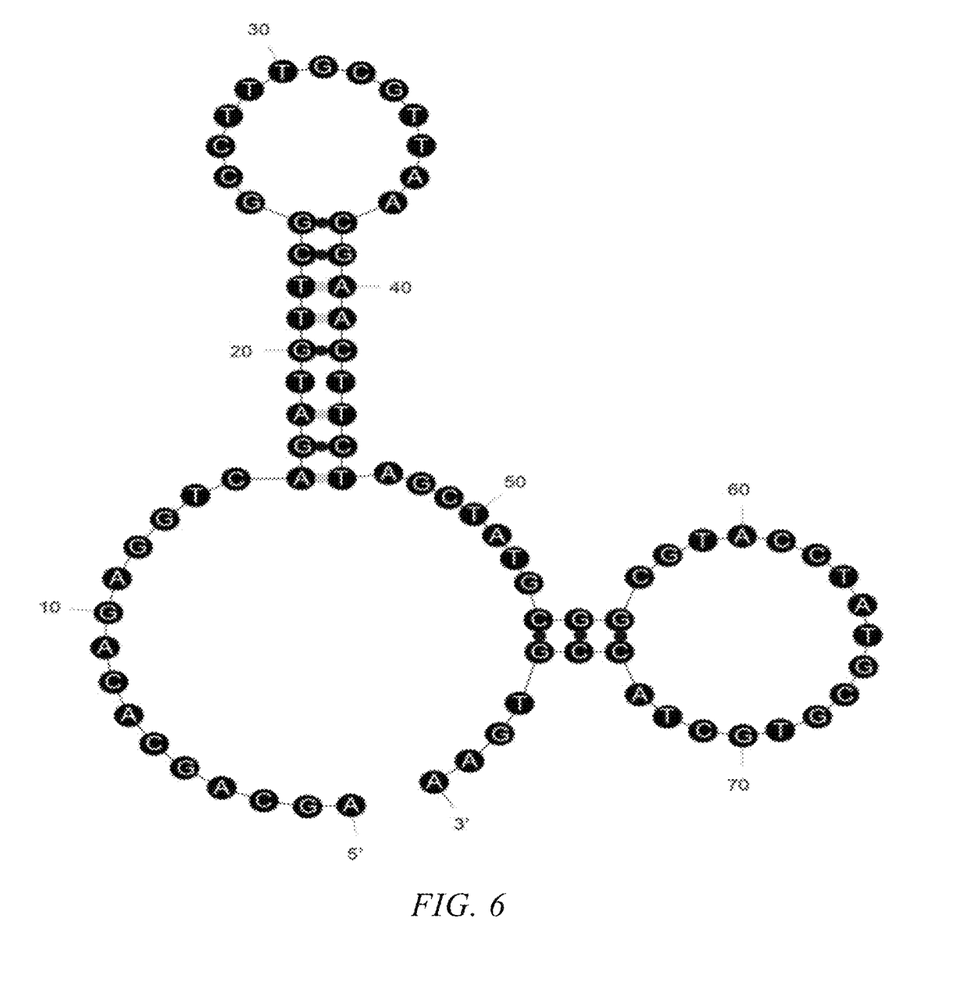
FIG. 6 shows a schematic diagram predicting the secondary structure of the nucleic acid aptamer Lg-18 in Example 5.

The aptamer sequence was introduced into Mfold, and the forming conditions of the secondary structure were set (Na$^+$: 100 mM; Mg$^{2+}$: 1 mM; 37° C.). The formed secondary structure is shown in FIG. 6, which has a typical stem-loop structure.

Example 6

Simulation of the Interaction Between the Aptamer Lg-18 and β-Lactoglobulin by Molecular Docking Preparation of the three-dimensional conformation of the aptamer: The Vienna format of the aptamer Lg-18 sequence was generated by the Mfold online tool, and then an optimal three-dimensional conformation of the corresponding sequence in the Vienna format was generated by the RNA-composer software.

Figure 7:
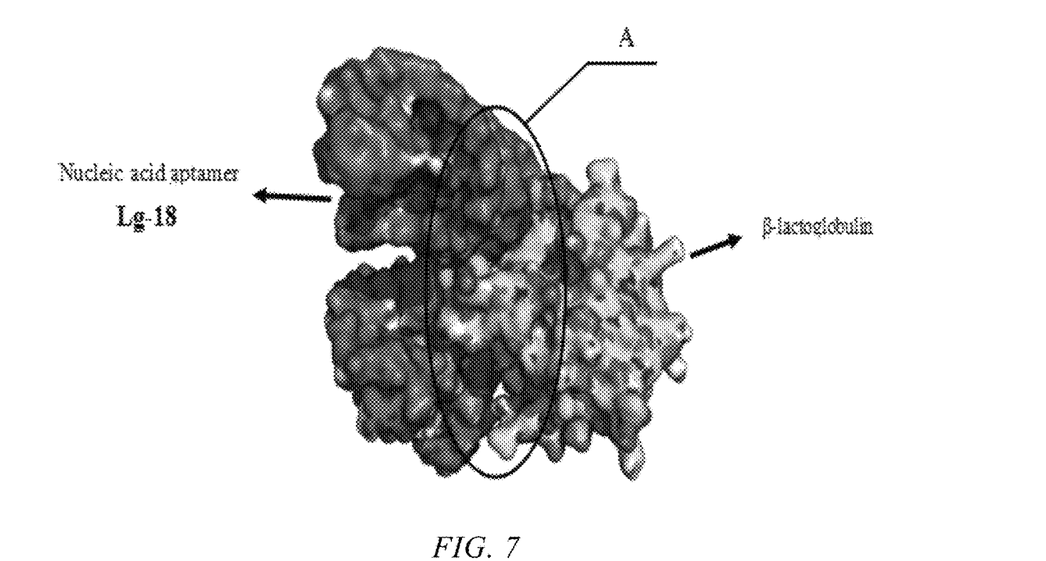
FIG. 7 is a schematic diagram showing the molecular docking between the nucleic acid aptamer Lg-18 and β-lactoglobulin in Example 6.
Figure 8:
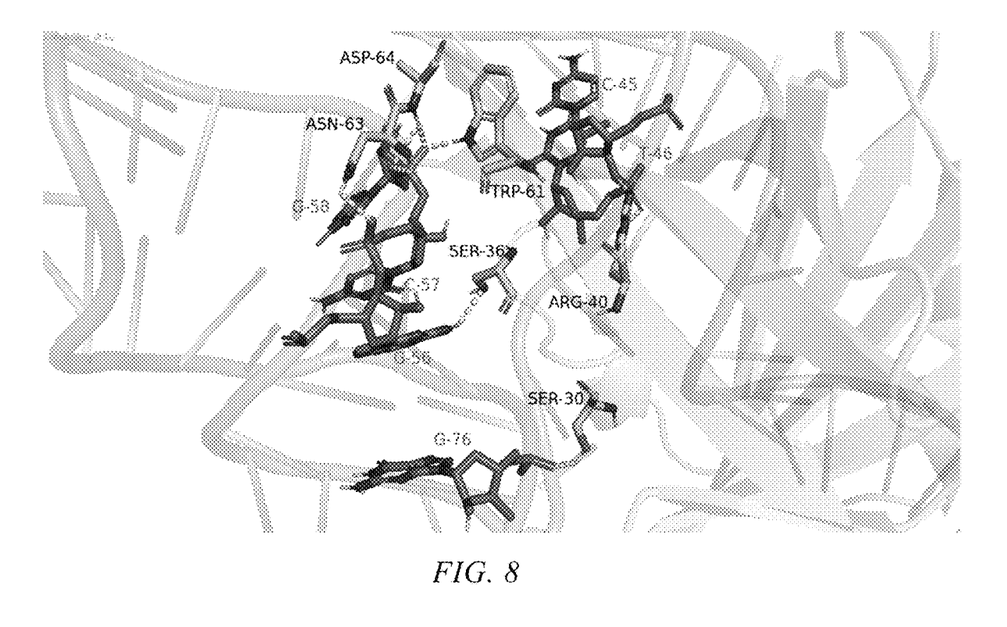
FIG. 8 is a map of the binding site of part A in FIG. 7.

Simulation of docking: The three-dimensional conformation of β-lactoglobulin (PDB: 2Q2M) was downloaded from the PDB website, and a series of pre-treatments including removing water molecules, adding non-polar hydrogen, and adding Kollman Charges were performed by the MGL Tools. Finally, a .pdbqt file was generated. The three-dimensional conformation of the aptamer Lg-18 was introduced as a ligand, and adding non-polar hydrogen and adding Kollman Charges were performed as described above. The docking was simulated by Autodock vina, to search for the optimum binding sites of the aptamer and β-lactoglobulin. The docking parameters are as follows:

receptor=lacg.pdbqt
ligand=apt.pdbqt
center_x=41.408
center_y=54.25
center_z=25.132
size_x=125
size_y=125
size_z=12
out=vina.pdbqt Analysis of docking results: After docking by Autodock vina, the binding sites of the aptamer Lg-18 and β-lactoglobulin was preliminarily determined. There are many binding modes with binding energy around −17 kcal/mol. One of these modes where there are a variety of hydrogen bonds between the two was analyzed for the binding sites by the pymol software. The results are shown in FIGS. 7 and 8. There is an intermolecular interaction between the nucleic acid aptamer Lg-18 and β-lactoglobulin, and hydrogen bonding is formed between C-45/T-46 and ARG-40, G-56 and SER-36, C-57 and ASN-63, G-58 and ASN-63/TRP-61, and G-76 and SER-30, which can be determined as the main binding region.

While the present invention has been described above by way of preferred examples, the present invention is not limited thereto. Various modifications and changes can be made by those skilled in the art without departing from the spirit and scope of the present invention as defined by the appended claims.

What is claimed is:

1. A nucleic acid aptamer specifically recognizing β-lactoglobulin, having a sequence as shown in SEQ ID NO:1.

2. The nucleic acid aptamer specifically recognizing β-lactoglobulin according to claim 1, wherein the sequence of the nucleic acid aptamer is modified by any one or more of phosphorylation, methylation, amination, sulfhydrylation, phosphorothioate modification, and side chain modification of glycosyl ring.

3. The nucleic acid aptamer specifically recognizing β-lactoglobulin according to claim 1, wherein the sequence of the nucleic acid aptamer is linked with any one or more of a fluorescent marker, a radioactive material, a therapeutic material, biotin, digoxin, a nano-luminescent material, a small peptide, siRNA and an enzyme marker.

4. The nucleic acid aptamer specifically recognizing β-lactoglobulin according to claim 1, wherein the sequence as shown in SEQ ID NO:1 has an intermolecular interaction with β-lactoglobulin, where hydrogen bonding is formed between C-45/T-46 and ARG-40, G-56 and SER-36, C-57 and ASN-63, G-58 and ASN-63/TRP-61, and G-76 and SER-30.

5. A kit, comprising the nucleic acid aptamer according to claim 1.

* * * * *